(12) United States Patent
Minami et al.

(10) Patent No.: US 11,739,360 B2
(45) Date of Patent: Aug. 29, 2023

(54) INTERLEUKIN-6, 10 PRODUCTION PROMOTER

(71) Applicant: ASAHI GROUP HOLDINGS, LTD., Tokyo (JP)

(72) Inventors: Taichi Minami, Ibaraki (JP); Yu Imai, Ibaraki (JP); Tetsuya Ishida, Ibaraki (JP); Junpei Yoshida, Ibaraki (JP); Takeshi Shirai, Ibaraki (JP)

(73) Assignee: ASAHI GROUP HOLDINGS, LTD., Tokyo (JP)

( * ) Notice: Subject to any disclaimer, the term of this patent is extended or adjusted under 35 U.S.C. 154(b) by 24 days.

(21) Appl. No.: 16/972,709

(22) PCT Filed: Jun. 3, 2019

(86) PCT No.: PCT/JP2019/021912
§ 371 (c)(1),
(2) Date: Dec. 7, 2020

(87) PCT Pub. No.: WO2020/003905
PCT Pub. Date: Jan. 2, 2020

(65) Prior Publication Data
US 2021/0254118 A1    Aug. 19, 2021

(30) Foreign Application Priority Data

Jun. 27, 2018  (JP) .................... 2018-121852

(51) Int. Cl.
C12P 21/06    (2006.01)
C12N 1/06    (2006.01)

(52) U.S. Cl.
CPC .............. *C12P 21/06* (2013.01); *C12N 1/063* (2013.01)

(58) Field of Classification Search
None
See application file for complete search history.

(56) References Cited

U.S. PATENT DOCUMENTS

2014/0328996 A1* 11/2014 Johal ................... A23K 40/00
426/523
2017/0107547 A1   4/2017 Speetjens et al.

FOREIGN PATENT DOCUMENTS

EP      3266863 A1 *  1/2018  ............ A23K 10/16
JP      2017-511122    4/2017

OTHER PUBLICATIONS

Sonck, Eva, et al. "The effect of β-glucans on porcine leukocytes." Veterinary immunology and immunopathology 135.3-4 (2010): 199-207 (Year: 2010).*
Běhalová, B., et al. "Comparison of various ways of extraction of nucleic acids and of preparation of yeast extract from *Saccharomyces cerevisiae* and Candida utilis." Acta biotechnologica 11.6 (1991): 547-552. (Year: 1991).*
International Preliminary Report on Patentability dated Jan. 7, 2021 in International (PCT) Patent Application No. PCT/JP2019/021912.
International Search Report (ISR) dated Jul. 9, 2019 in International (PCT) Application No. PCT/JP2019/021912.
K.W. Yu et al., "Physiological effects of yeast hydrolysate SCP-20", Food Research International, vol. 35, No. 9, pp. 879-884, 2002.
Huan-sheng Yang et al., "Effects of yeast products on the intestinal morphology, barrier function, cytokine expression, and antioxidant system of weaned piglets", Journal of Zhejiang University Science B, vol. 17, No. 10, pp. 752-762, 2016.
Sarah Walachowski et al., "Triggering Dectin-t-Pathway Alone Is Not Sufficient to Induce Cytokine Production by Murine Macrophages", https://www.ncbi.nlm.nih.gov/pubmed/?term=Triggering+dectin1+pathway+alone+is+not+sufficient, cited in the specification.
Extended European Search Report dated Apr. 4, 2022 in corresponding European Patent Application No. 19825767.7.
Samir Jawhara et al: "Modulation of Intestinal Inflammation by Yeasts and Cell Wall Extracts: Strain Dependence and Unexpected Anti-Inflammatory Role of Glucan Fractions", PLos One, vol. 7, Issue 7, Jul. 2012.

\* cited by examiner

*Primary Examiner* — Robert J Yamasaki
(74) *Attorney, Agent, or Firm* — Wenderoth, Lind & Ponack, L.L.P.

(57) ABSTRACT

[Problem] To provide a novel technology that can promote the production of interleukin-6, and to provide a novel technology that can promote the production of interleukin-10.

[Solution] Provided are an interleukin-6 production promoter that comprises a crude yeast cell wall hydrolysate, and an interleukin-10 production promoter that comprises a crude yeast cell wall hydrolysate.

2 Claims, 2 Drawing Sheets

INTERLEUKIN-6, 10 PRODUCTION PROMOTER

TECHNICAL FIELD

The present invention relates to interleukin-6, 10 production.

BACKGROUND ART

Attacks of the immune system against pathogens that have invaded the body include phagocytosis by phagocytes such as neutrophils and macrophages (innate immune system), the disruption of host cells by the release of cytotoxic substances such as perforin from cytotoxic T cells, and the inactivation of pathogens by antibodies produced by B cells (adaptive immune system).

Cytokines play important roles in the activation and the functional inhibition of cells involved in the immune system and such cytokines include interleukins secreted by leukocytes.

A plurality of interleukins has been identified up to now. Among them, interleukin-6 (IL-6) is known to have actions such as induction of acute reactions by stimulating macrophages. Interleukin-10 (IL-10) is known to be mainly produced by type 2 helper T cells (Th2) and act on inhibition of inflammatory reactions.

Meanwhile, the immunopotentiating effect of β-glucan, obtained by centrifugal purification after hydrolysis or an enzymatic treatment of yeast cell walls, has been reported (Non Patent Literature 1).

CITATION LIST

Non Patent Literature

Non Patent Literature 1 https://www.ncbi.nlm.nih.gov/pubmed/?term=Triggering+dectin1+pathway+alone+is+not+sufficient

SUMMARY OF INVENTION

Technical Problem

An object of the present invention is to provide a novel technique that makes it possible to promote production of interleukin-6. Another object of the present invention is to provide a novel technique that makes it possible to promote production of interleukin-10.

Solution to Problem

The present inventors have studied diligently and, as a result, found that crude state yeast cell wall hydrolysates have higher potency to promote production of interleukin-6 and interleukin-10 in comparison with purified yeast cell wall hydrolysates, thereby completing the present invention.

The gist of the present invention is as follows.

[1] An interleukin-6 production promoter comprising a crude yeast cell wall hydrolysate.
[2] The interleukin-6 production promoter according to [1], wherein the yeast cell wall hydrolysate is a yeast cell wall hydrolysate obtained by adjusting pH of yeast cell walls to 8.0 to 14.0 and hydrolyzing the yeast cell walls at 60 to 120° C. for 3 to 24 hours.
[3] An interleukin-10 production promoter comprising a crude yeast cell wall hydrolysate.
[4] The interleukin-10 production promoter according to [3], wherein the yeast cell wall hydrolysate is a yeast cell wall hydrolysate obtained by adjusting pH of yeast cell walls to 8.0 to 14.0 and hydrolyzing the yeast cell walls at 60 to 120° C. for 3 to 24 hours.
[5] Use of a crude yeast cell wall hydrolysate for preparing a composition that promotes production of interleukin-6.
[6] The use according to [5], wherein the yeast cell wall hydrolysate is a yeast cell wall hydrolysate obtained by adjusting pH of yeast cell walls to 8.0 to 14.0 and hydrolyzing the yeast cell walls at 60 to 120° C. for 3 to 24 hours.
[7] Use of a crude yeast cell wall hydrolysate for preparing a composition that promotes production of interleukin-10.
[8] The use according to [7], wherein the yeast cell wall hydrolysate is a yeast cell wall hydrolysate obtained by adjusting pH of yeast cell walls to 8.0 to 14.0 and hydrolyzing the yeast cell walls at 60 to 120° C. for 3 to 24 hours.
[9] The use according to any one of [5] to [8], wherein the composition is a food composition or a pharmaceutical composition.
[10] Non-therapeutic use of a yeast cell wall hydrolysate for promoting production of interleukin-6.
[11] The use according to [10], wherein the yeast cell wall hydrolysate is a yeast cell wall hydrolysate obtained by adjusting pH of yeast cell walls to 8.0 to 14.0 and hydrolyzing the yeast cell walls at 60 to 120° C. for 3 to 24 hours.
[12] Non-therapeutic use of a crude yeast cell wall hydrolysate for promoting production of interleukin-10.
[13] The use according to [12], wherein the yeast cell wall hydrolysate is a yeast cell wall hydrolysate obtained by adjusting pH of yeast cell walls to 8.0 to 14.0 and hydrolyzing the yeast cell walls at 60 to 120° C. for 3 to 24 hours.
[14] A method for promoting production of interleukin-6 in a subject, comprising ingesting a crude yeast cell wall hydrolysate.
[15] The method according to [14], wherein the yeast cell wall hydrolysate is a yeast cell wall hydrolysate obtained by adjusting pH of yeast cell walls to 8.0 to 14.0 and hydrolyzing the yeast cell walls at 60 to 120° C. for 3 to 24 hours.
[16] A method for promoting production of interleukin-10 in a subject, comprising ingesting a crude yeast cell wall hydrolysate.
[17] The method according to [16], wherein the yeast cell wall hydrolysate is a yeast cell wall hydrolysate obtained by adjusting pH of yeast cell walls to 8.0 to 14.0 and hydrolyzing the yeast cell walls at 60 to 120° C. for 3 to 24 hours.

Advantageous Effects of Invention

According to the present invention, a novel technique that makes it possible to promote production of interleukin-6 can be provided. Moreover, according to the present invention, a novel technique that makes it possible to promote production of interleukin-10 can be provided.

DESCRIPTION OF EMBODIMENT

Figure 1:
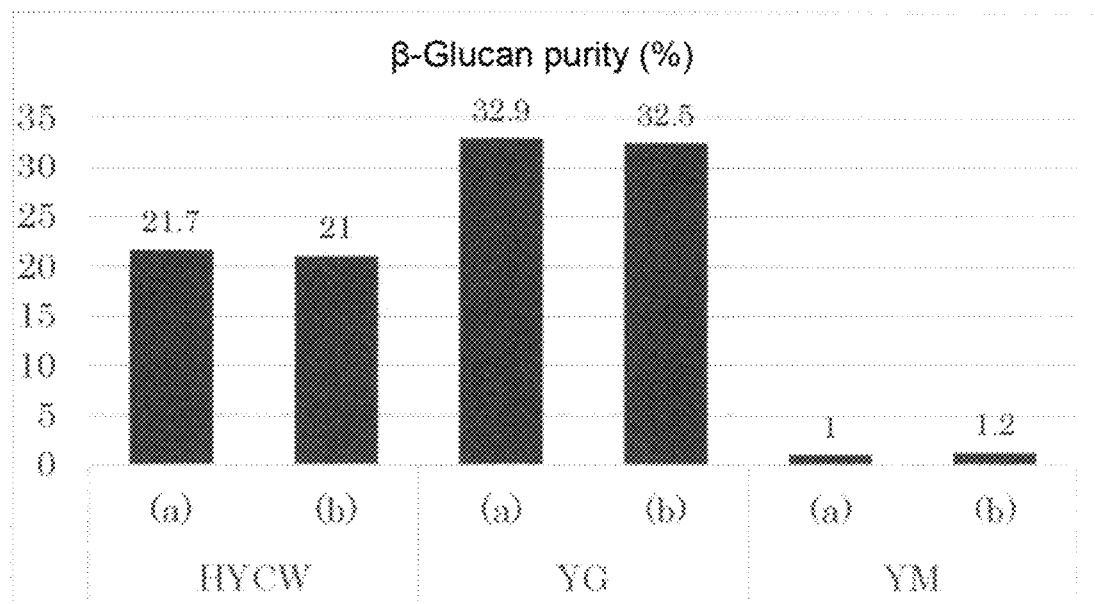
FIG. 1 is a graph of β-glucan purity of Examples.

One aspect of the present invention relates to an interleukin-6 (IL-6) production promoter. Another embodiment of the present invention relates to an interleukin-10 (IL-10) production promoter. Herein, these are generically referred to as IL-production promoters and one embodiment common to them will be described in detail below.

The IL-production promoters contain a crude yeast cell wall hydrolysate.

The crude yeast cell wall hydrolysate can be obtained by subjecting yeast cell walls to a hydrolysis treatment. The yeast cell walls that is used may be a commercially available product or prepared from yeast cells.

The method for obtaining the yeast cell walls from yeast cells is not particularly limited, but, for example, the yeast cell walls can be obtained from yeast cells by a known method. Specific examples thereof include a method involving heating yeast cells to 45 to 65° C. to allow the cells to autodigest for 5 to 20 hours and then removing supernatant with a centrifuge, a method involving killing yeast cells by heating to 80° C. or a higher temperature and then removing supernatant by centrifugation as they are, and a method involving addition of an enzyme to yeast cells, reaction with the enzyme and the yeast cells, and subsequent centrifugation and removal of supernatant.

The yeast which the yeast cell walls are derived from is not particularly limited, but can be determined by a person skilled in the art as appropriate. Examples thereof include food grade products of yeasts that belong to the genus *Saccharomyces*, the genus *Kluyveromyces*, the genus *Candida*, the genus *Pichia*, and the genus *Torulopsis* (Bekatorou et al., 2006, Food Technol. Biotechnol. 44(3), 407-415).

Among them, yeasts belonging to the genus *Saccharomyces* such as brewer's yeast are preferred in terms of promoting more production of IL-6 and IL-10. Examples of the yeasts belonging to the genus *Saccharomyces* include brewer's yeasts, whiskey yeasts, shochu yeasts, baker's yeasts, wine yeasts, and sake yeasts, and, for example, one or more of them may be used for preparation of the yeast cell wall hydrolysate.

When a brewer's yeast is used, examples of the yeast cell walls include yeast cell wall preparations from slurry brewer's yeast, compressed brewer's yeast, dry brewer's yeast, and brewer's yeast suspensions.

The method for hydrolyzing the yeast cell walls is not particularly limited, but can be determined by a person skilled in the art as appropriate.

Among them, preferred embodiments, in terms of further promotion of the amount of IL-6 and IL-10 production, include adjusting pH of yeast cell walls to 8.0 to 14.0 (more preferably 10.0 to 12.0) and hydrolyzing the yeast cell walls at 60 to 120° C. (more preferably 85 to 95° C.) for 3 to 24 hours (more preferably 12 to 20 hours). In the hydrolysis, stirring is not necessary.

Moreover, the yeast cell walls to be hydrolyzed may be subjected to a washing treatment under alkaline conditions before the hydrolysis treatment, as needed.

The IL-production promoters comprise a crude yeast cell wall hydrolysate that can be obtained, for example, as described above. The term "crude" refers to a state in which the product has not been subjected to a step for increasing purity of a specific component in the yeast cell walls, for example, β-glucan, or mannan. Examples of the step for the purpose of increasing purity of a specific component in the yeast cell walls include steps of centrifugation, filtration, distillation, recrystallization, extraction, sublimation, chromatography, separation by isoelectric precipitation, separation by ethanol precipitation, and salt precipitation of the yeast cell wall hydrolysate obtained as described above. However, steps similar to these, but not for the purpose of increasing purity of a specific component in yeast cell walls, for example, steps for the purpose of removing contaminated substances to secure quality as a food or drink, are not included. Those skilled in the art can determine whether a step is for increasing purity of a specific component in a yeast cell wall hydrolysate, from equipment or treatment conditions used in the step.

In addition to the crude yeast cell wall hydrolysate, the IL-production promoters may comprise other components, as long as they allow the purpose of the present invention to be achieved.

The form (dosage form) of the IL-production promoters is not particularly limited and they can be produced as a pharmaceutical preparation, a quasi-drug, or a food or drink.

When the IL-production promoters are to be provided in a pharmaceutical preparation, a quasi-drug, or a food or drink, the crude yeast cell wall lysate may be mixed with, for example, a filler, a binder, a stabilizer, a disintegrant, a lubricant, a corrigent, a suspending agent, a coating, or any other components, as appropriate, to be formulated into such a formulation. Possible dosage forms include tablets, pills, capsules, granules, powder, powdered drugs, and syrups and these are preferably administered orally.

Alternatively, when the IL-production promoters are manufactured in the aspect of a food or drink, the food or drink is not particularly limited, but it may be a food for special dietary uses such as a food for specified health uses or a functional nutritional food, as well as a usual food or drink. Specific examples of the food or drink include dietary supplements (supplements), bovine milk, processed milk, milk beverages, refreshing beverages, fermented milk, yogurt, cheese, bread, cookies, crackers, pizza crusts, ice creams, candies, gummy candies, chewing gum, infant formula, fluid diets, foods for invalids, foods such as powdered milk for infants, and foods such as powdered milk for nursing mothers.

Moreover, the IL-production promoters are not limited to pharmaceutical preparations, quasi drugs, foods and drinks for humans, but may be in a form of a pharmaceutical preparation or a feeding-stuff for animals other than humans. Examples of the animals other than humans include higher vertebrates other than humans and, in particular, mammals other than humans, and more specific examples include pets such as dogs and cats and domestic animals such as cows, horses, pigs, and sheep. Moreover, birds and fishes are also included and more specific examples include meat chicken, egg chicken, and turkey; and farmed fish such as salmon, carp, crucian carp, tilapia, catfish, sea bass, yellowtail, amberjack, flatfish, sea bream, and tuna. Furthermore, invertebrates such as shrimp and crabs are also included.

The daily intake of IL-production promoters is not particularly limited as well, and the content of the crude yeast cell wall hydrolysate may be adjusted so that an adult can ingest, for example, 0.01 to 100 g, preferably 0.1 to 10 g thereof per day. The content percentage of the crude yeast cell wall hydrolysate in the IL-production promoters is not particularly limited as well and it may be adjusted as appropriate depending on the easiness of production, the preferred daily dose, or the like.

According to the foregoing embodiment, a novel technique that makes it possible to promote production of IL-6 and/or IL-10 can be provided.

Production of IL-6 and/or IL-10 can be promoted by ingesting the crude yeast cell wall hydrolysate according to the embodiment, without limiting the aspect of ingestion, for example, in an aspect of a pharmaceutical preparation, a quasi-drug, or a food comprising the crude yeast cell wall hydrolysate described above. As a result, palliation of symptoms of infections by activation of the immune function and the like can be expected with some individual differences.

EXAMPLES

The present invention will be described in more detail with reference to Examples below. However, the present invention is not limited thereto.

Preparation of Crude Yeast Cell Wall Lysates (Examples)

Yeast cell walls (10% solid contents) derived from a brewer's yeast, which belongs to the genus *Saccharomyces*, produced at Asahi Group Foods, Ltd. Tochigi Koganei Factory were subjected to a hydrolysis treatment.

Specifically, the yeast cell walls were adjusted to pH 11 with sodium hydroxide, then heated to 90° C., and treated for 18 hours. These were dried with a drum dryer to obtain yeast cell wall hydrolysates (hereinafter, HYCW).

Preparation of Purified Yeast Cell Wall Lysates (Comparative Examples)

Without drying after the aforementioned hydrolysis treatment, the hydrolysates were adjusted to pH 5.5 with hydrochloric acid and then centrifuged to obtain heavy solutions. The heavy solutions were dried with a drum dryer to obtain yeast glucan (hereinafter, YG). The light solutions were concentrated to Brix 40%, then sterilized under conditions at 125° C. for 40 seconds, and dried by spray drying to obtain yeast mannan (hereinafter, YM).

Both Examples and Comparative Examples were prepared as described above by using two lots of yeast cell walls produced in August, 2013 and in September of the year. Hereinafter, those derived from the yeast cell walls produced in August, 2013 are designated as (a) and those derived from the yeast cell walls produced in September of the year are designated as (b).

[β-Glucan Purity]

Collected samples of Examples HYCW and Comparative Examples YG and YM were treated in order with α-amylase, protease, and amyloglucosidase and then ethanol was added thereto. The generated precipitates were washed with 80% ethanol and acetone. Subsequently, 5 mL of 72% sulfuric acid was added and degradation was performed at 20° C. for 4 hours. 70 mL of water was then added and hydrolysis was performed for 2 hours in a boiling water bath. After cooling and neutralization, the glucose concentration was quantified by the glucose oxidase method and the concentration was multiplied by 0.9 to calculate the purity of β-glucan.

The results are shown in FIG. 1. HYCW can be divide into a β-glucan fraction and a mannan fraction by centrifugation. YG was obtained by drying the precipitate and β-glucan purity thereof was increased to approximately 33%, while YM was obtained by drying the supernatant and β-glucan was hardly contained and the purity thereof was approximately 1%.

[Measurement of Amounts of IL-6 and IL-10 Production]

IL-6 and IL-10 were measured according to a known method (Sonck et al., 2010, Veterinary Immunology and Immunopathology 135, 199-207). Peripheral blood was collected into heparin tubes from the jugular vein of 5 weaning piglets at 14 weeks of age. Subsequently, peripheral blood mononuclear cells (PBMCs) were obtained by density gradient centrifugation under conditions at 800×g at 18° C. for 25 minutes using Lymphoprep. Erythrocytes were hemolyzed with ammonium chloride and centrifugation was performed at 350×g at 18° C. for 10 minutes and then the precipitation was washed three times with the RPMI1640 medium containing 10% fetal bovine serum, a solution of non-essential amino acids, 100 µg/mL sodium pyruvate, 292 mg/mL L-glutamine, 100 IU/mL penicillin, 100 µg/mL streptomycin, and 100 µg/mL kanamycin and suspended to $10^7$ cells/mL.

Peripheral blood mononuclear cells (PBMCs) were stimulated with HYCW, YG, or YM and the amounts of IL-6 and IL-10 production were measured.

Specifically, $1 \times 10^7$ cells of PBMCs were stimulated with samples at 20 µg/mL or 200 µg/mL on a multi-well plate for 24 hours.

Subsequently, the supernatant was collected and measured with a commercially available cytokine measurement ELISA kit (R&D Systems, Inc.) according to the manual. HBSS (Hank's Balanced Salt Solution) was used as a negative control.

Figure 2:
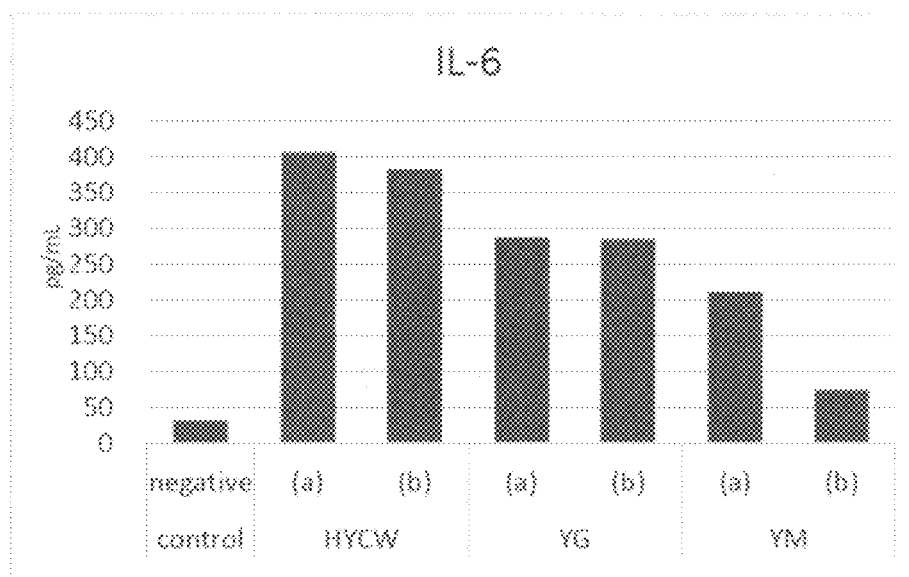
FIG. 2 is a graph illustrating amounts of IL-6 production in Examples.
Figure 3:
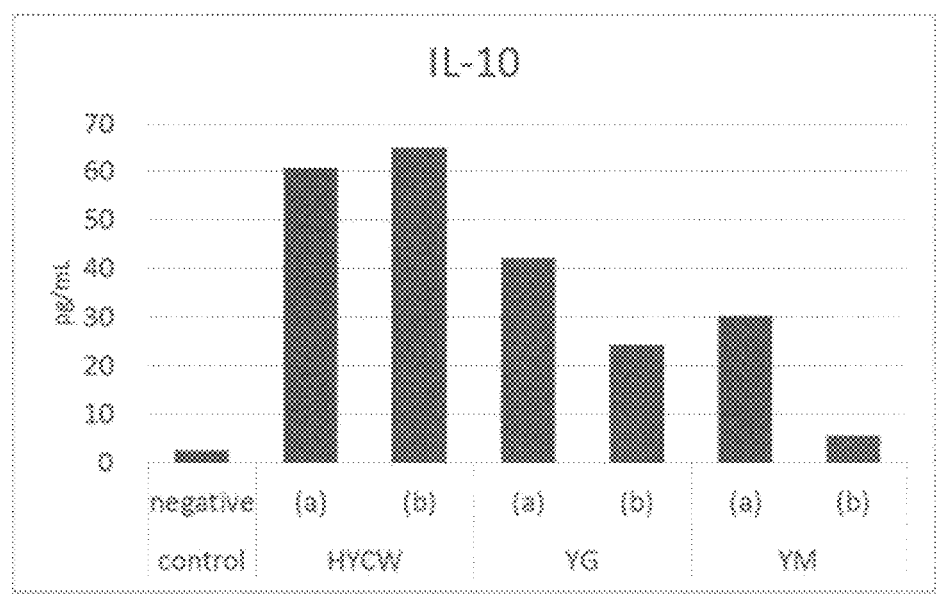
FIG. 3 is a graph illustrating amounts of IL-10 production in Examples.

The results are shown in FIGS. 2 and 3.

As seen in FIGS. 2 and 3, it is found that the amounts of IL-6 and IL-10 production were greatly increased by stimulation with HYCW in comparison with those with YG or YM.

The invention claimed is:

1. A method for promoting interleukin-6 production in a subject, which comprises:
    administering a yeast cell wall hydrolysate including β-glucan and mannan to the subject,
    wherein the yeast cell wall hydrolysate is obtained by a hydrolysis treatment to yeast cell walls, the yeast cell walls having been obtained by autodigesting yeast cells, killing yeast cells by heating or reacting yeast cells with an enzyme, and then subsequently centrifuging and discarding supernatant, thereby resulting in the yeast cell walls,
    wherein the yeast cell wall hydrolysate is a yeast cell wall hydrolysate obtained by adjusting pH of yeast cell walls to 10.0 to 14.0 and hydrolyzing the yeast cell walls at 60 to 120° C. for 3 to 24 hours.

2. A method for promoting interleukin-10 production in a subject, which comprises:
    administering a yeast cell wall hydrolysate including β-glucan and mannan to the subject,
    wherein the yeast cell wall hydrolysate is obtained by a hydrolysis treatment to yeast cell walls, the yeast cell walls having been obtained by autodigesting yeast cells, killing yeast cells by heating or reacting yeast cells with an enzyme, and then subsequently centrifuging and discarding supernatant, thereby resulting in the yeast cell walls,
    wherein the yeast cell wall hydrolysate is a yeast cell wall hydrolysate obtained by adjusting pH of yeast cell walls to 10.0 to 14.0 and hydrolyzing the yeast cell walls at 60 to 120° C. for 3 to 24 hours.

* * * * *